United States Patent [19]

Ito et al.

[11] Patent Number: 5,698,490
[45] Date of Patent: *Dec. 16, 1997

[54] THERMAL TRANSFER INK RIBBONS USING THE SAME

[75] Inventors: Kengo Ito; Masanobu Hida; Kaori Isaji, all of Kanagawa, Japan

[73] Assignee: Sony Corporation, Tokyo, Japan

[*] Notice: The term of this patent shall not extend beyond the expiration date of Pat. No. 5,356,854.

[21] Appl. No.: 506,146

[22] Filed: Jul. 24, 1995

Related U.S. Application Data

[63] Continuation-in-part of Ser. No. 336,155, Nov. 8, 1994, abandoned, which is a continuation-in-part of Ser. No. 95,877, Jul. 22, 1993, abandoned.

[51] Int. Cl.$^6$ .................. B41M 5/035; B41M 5/38
[52] U.S. Cl. .................. 503/227; 428/195; 428/913; 428/914
[58] Field of Search .................. 8/471; 428/195, 428/480, 913, 914; 503/227

[56] References Cited

U.S. PATENT DOCUMENTS

| | | | |
|---|---|---|---|
| 494,838 | 4/1893 | Bender | 544/103 |
| 2,741,605 | 4/1956 | Zwilgmeyer et al. | 260/244 |
| 3,379,723 | 4/1968 | Clarke et al. | 260/240.9 |
| 4,559,273 | 12/1985 | Kutsukake et al. | 428/484 |
| 4,602,263 | 7/1986 | Borror et al. | 503/201 |
| 4,666,320 | 5/1987 | Kobayashi et al. | 400/241.1 |
| 4,748,149 | 5/1988 | Byers | 503/227 |
| 5,356,854 | 10/1994 | Ito | 503/227 |

FOREIGN PATENT DOCUMENTS

| | | |
|---|---|---|
| SHO34-694 | 2/1959 | Japan. |
| SHO40-19951 | 9/1965 | Japan. |
| SHO45-25788 | 8/1970 | Japan. |
| SHO45-28024 | 9/1970 | Japan. |
| SHO47-4881 | 3/1972 | Japan. |
| SHO47-13638 | 7/1972 | Japan. |
| SHO50-7087 | 3/1975 | Japan. |
| SHO50-149723 | 12/1975 | Japan. |
| BP13565/90 | of 1891 | United Kingdom. |
| BP18623/90 | of 1891 | United Kingdom. |

Primary Examiner—Bruce H. Hess
Attorney, Agent, or Firm—Hill, Steadman & Simpson

[57] ABSTRACT

When the counter ion of hydrophilic cationic dyes is substituted with an organic anion including a sulfosuffinate anion such as diethylhexylsulfonate anion, an alkylbenzenesulfonate anion such as a dodecylbenzenesulfonate, an alkylsulfate anion such as a laurylsulfate anion, or a soap anion such as a laurylsulfate anion, the cationic dyes are imparted with hydrophobicity. An ink layer 3 containing the hydrophobic cationic dye is formed on a support 2 to provide a thermal transfer ink ribbon 10.

7 Claims, 13 Drawing Sheets

3 INK LAYER
10 THERMAL TRANSFER INK RIBBON
2 SUPPORT
1 HEAT-RESISTANT LUBLICATING LAYER

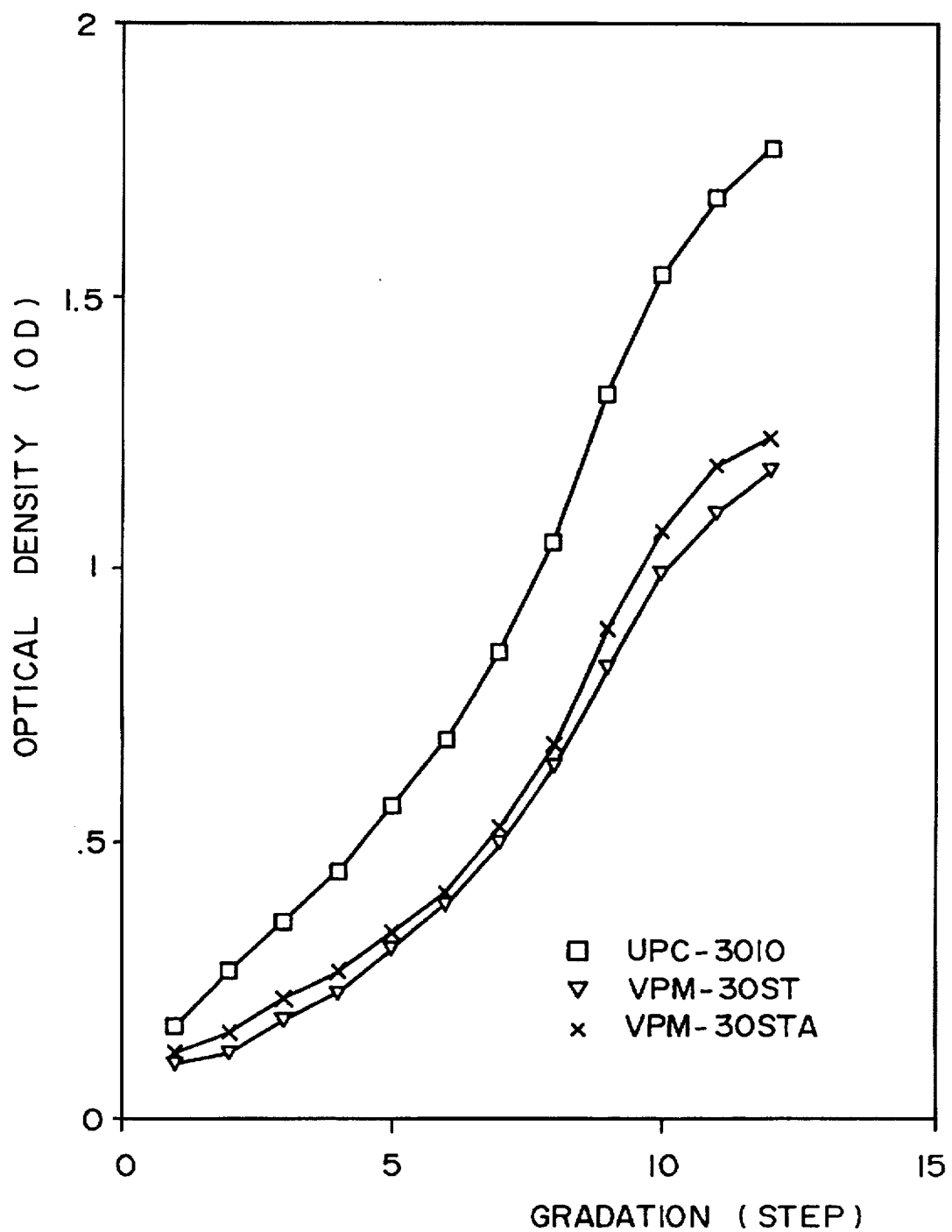
F I G. 2

F I G. 3
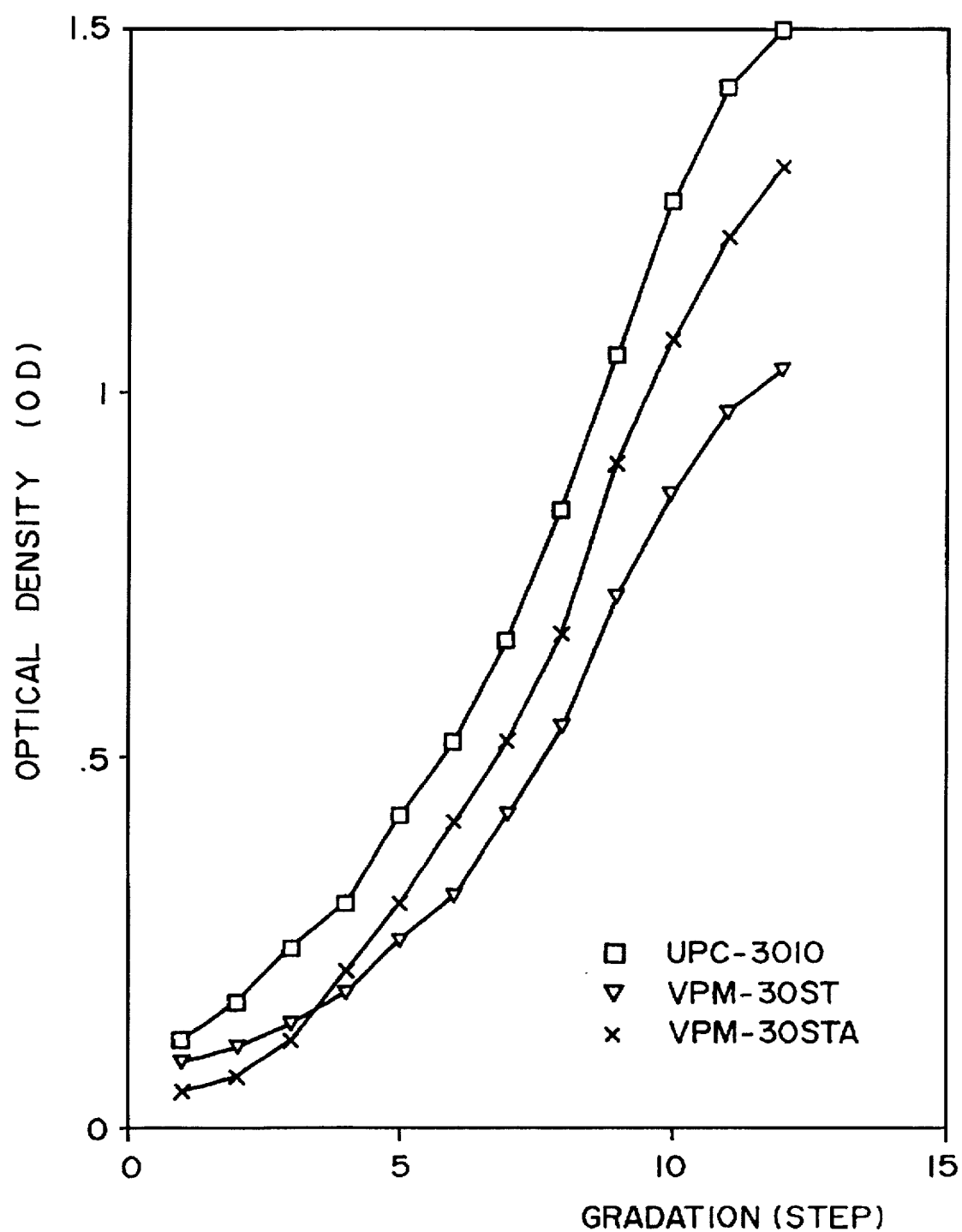

THERMAL TRANSFER INK RIBBONS USING THE SAME

This application is a continuation-in-part of U.S. Ser. No. 08/336,155 filed Nov. 8, 1994 entitled Thermal Transfer Ink Ribbons Using The Same (abandoned) which is a continuation-in-part of U.S. Ser. No. 08/095,877 filed Jul. 22, 1993 (abandoned) both of which are hereby incorporated by reference.

FIELD OF THE INVENTION

This invention relates to hydrophobic cationic dyes which are adapted for use in image formation by a thermal transfer system and also to thermal transfer ink ribbons.

BACKGROUND

In recent years, video printers for obtaining hard copies of images from video signals have been intensively developed. The images have been formed according to thermal transfer systems. More particularly, an ink ribbon comprised on a polyethylene terephthalate substrate and an ink layer formed by mixing a dye with or dissolving the dye in a hydrophobic polymer is provided. The ink layer is superposed in a dye-receiving hydrophobic polymer layer of a transfer material formed on a synthetic paper, under which the ink ribbon is heated according to image signals by means of a thermal head or the like. As a result, a disperse dye in the ink layer is thermally transferred to the dye-receiving layer to form an image. As the dyes of the thermal transfer ink ribbons which are employed in the thermal transfer system, sublimable dyes have been heretofore considered principally favorable from the standpoint of the image formation. According to recent investigative trends wherein types of materials have been taken into account, importance is placed on thermal diffusing properties rather than sublimability. Moreover, there are other important properties or factors of the dyes including miscibility with hydrophobic polymers used in the ink layer of the thermal transfer ink ribbon, dyeability against the dye-receiving layer consisting of hydrophobic polymers of the transfer material, and a degree of achievement of actual sensitivity at the time of the thermal transfer. To this end, disperse dyes have been frequently used as a dye for the thermal transfer ink ribbons.

However, when disperse dyes are used as the dye for thermal transfer ink ribbons, there arises the problem that they are unsatisfactory in practical utility from the standpoint of the sensitivity during the transfer operations and the hue and light fastness of the resultant images.

To avoid this, it may occur that cationic dyes which are known for dyeing acrylic fibers as having an inherent brightness, high coloring properties and good light fastness are used for the thermal transfer ribbons. Although the cationic dyes exhibit good light fastness and wet fastness, they are hydrophilic in nature, so that it is difficult to uniformly, stably keep the dye in butyryl resins ordinarily used as the binder of the ink layer of thermal transfer ink ribbons. Thus, it has not been possible for cationic dye to be used in the thermal transfer ink ribbon.

SUMMARY OF THE INVENTION

One object of this invention is to provide dyes which can be mixed with hydrophobic polymers satisfactorily and uniformly with good storage stability.

Another object of this invention is to improve sensitivity at the time of the transfer and the color and light fastness of the resultant images by the use of the dyes of this invention to form an ink layer of a thermal transfer ink ribbon.

According to one aspect of this invention, there is provided a hydrophobic cationic dye which is obtained by substituting, with an organic anion, a counter ion of a diazacarbocyanine cationic dye of the following formula (1).

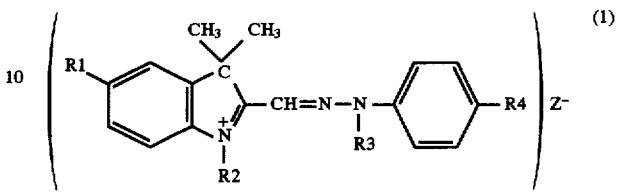

In the formula (1), R1, R2, R3 and R4 are independently represented by one of the first group including a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group. The hydrocarbon of the alkyl group, the cycloalkyl group, the alkoxy group, the aryl group, the aryloxy group, the aralkyl group, the aralkoxy group, the alkenyl group, the alkenoxy group, the alkoxycarbonyl group, the acyloxy group or the acyl group of the first group may be saturated aliphatic hydrocarbon, unsaturated aliphatic hydrocarbon, alicyclic hydrocarbon, aromatic hydrocarbon or the combination of the same. Further, a part of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the second group including a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group or the like. Furthermore a hydrogen of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the third group including a halogen atom, a silicon atom, a phosphorous atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group or the like. In the formula (1), Z- represents a counter ion.

BRIEF DESCRIPTION OF THE DRAWINGS

FIG. 2 is a dynamic sensitivity characteristic graph of an ink ribbon of the invention.

FIG. 3 is a dynamic sensitivity characteristic graph of another ink ribbon of the invention.

DESCRIPTION OF THE PREFERRED EMBODIMENTS

Figure 1:
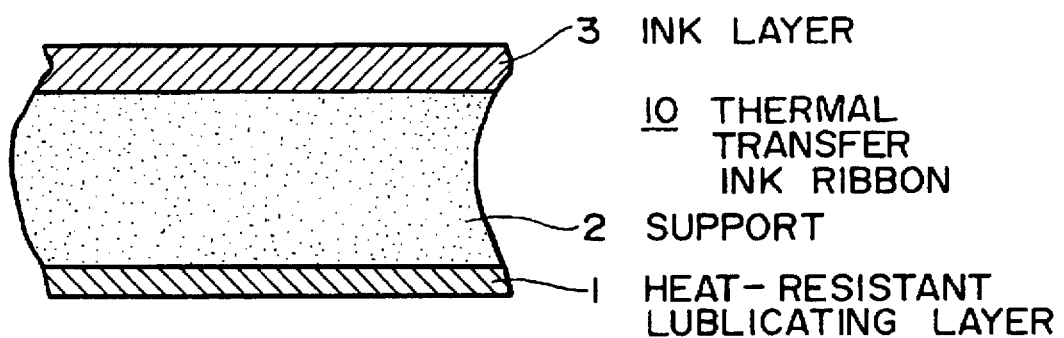
FIG. 1 shows a sectional view of a thermal transfer ink ribbon of the invention.

We have found that the substitution of a counter ion, such as a halogen, of cationic dyes with an organic anion enables the cationic dyes to be imparted with hydrophobicity and that specific type of dyes have good gradation properties with respect to yellow, magenta and cyan colors necessary for the formation of full color images. The invention is accomplished based on this finding.

The invention provides as a yellow dye, a hydrophobic cationic dye which is obtained by substituting, with an organic anion, a counter ion of a diazacarbocyanine cationic dye of the following formula (1).

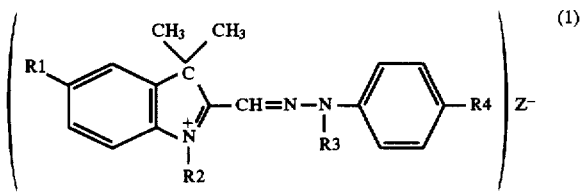

In the formula (1), R1, R2, R3 and R4 are independently represented by one of the first group including a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group. The hydrocarbon of the alkyl group, the cycloalkyl group, the alkoxy group, the aryl group, the aryloxy group, the aralkyl group, the aralkoxy group, the alkenyl group, the alkenoxy group, the alkoxycarbonyl group, the acyloxy group or the acyl group of the first group may be saturated aliphatic hydrocarbon, unsaturated aliphatic hydrocarbon, alicyclic hydrocarbon, aromatic hydrocarbon or the combination of the same. Further, a part of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the second group including a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group or the like. Furthermore a hydrogen of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the third group including a halogen atom, a silicon atom, a phosphorous atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group or the like. In the formula (1), Z- represents a counter ion.

Examples of the cationic yellow dyes not substituted with an organic anion include C.I. Basic Yellow 28, 51 and the dye disclosed in Japan issued patent SHO 47-4881 which is incorporated by reference.

Another type of yellow dye provided according to the invention includes hydrophobic cationic dyes which are obtained by substituting the counter ion of a cationic dye such as C.I. Basic Yellow 21, 36, 67 or 73 with an organic anion.

The invention also provides as a magenta dye, a hydrophobic cationic dye which is obtained by substituting, with an organic anion, a counter ion of a hemicyanine cationic dye of the following formula (2).

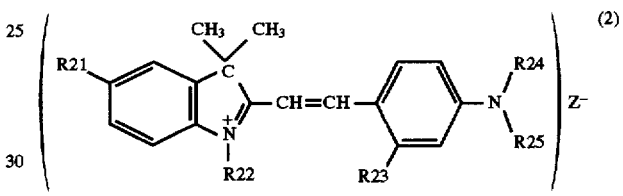

In the formual (2), R21, R22, R23, R24 and R25 are independently represented by one of the first group including a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group. The hydrocarbon of the alkyl group, the cycloalkyl group, the alkoxy group, the aryl group, the aryloxy group, the aralkyl group, the aralkoxy group, the alkenyl group, the alkenoxy group, the alkoxycarbonyl group, the acyloxy group or the acyl group of the first group may be saturated aliphatic hydrocarbon, unsaturated aliphatic hydrocarbon, alicylic hydrocarbon, aromatic hydrocarbon or the combination of the same. Further, a part of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the second group including a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group or the like. Furthermore a hydrogen of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the third group including a halogen atom, a silicon atom, a phosphorous atom; an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group or the like. In the formula (2), Z- represents a counter ion. R24 and R25 may join together to form a ring.

Examples of the cationic magenta dyes prior to substitution with an organic anion include C.I. Basic Red 13, 14, C.I. Basic Violet 7, 16, C.I. 48025, 48030, and the dye disclosed in Japan issued patents SHO 34-694, SHO 40-19951, SHO 45-28024, SHO 50-7087, Japanese Laid-Open Patent SHO 50-149723 and U.S. Pat. No. 3,379,723 which is incorporated by reference.

Moreover, the invention provides as a cyan dye, a hydrophobic cationic dye which is obtained by substituting, with an organic anion, a counter ion of an oxazine cationic dye of the following formula (3a) or (3b).

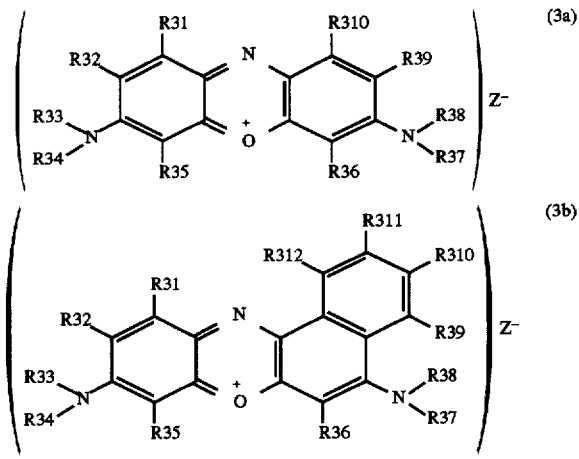

In the formula (3a) and (3), R31, R32, R33, R34, R35, R36, R37, R38, R39, R310, R311 and R312 are independently represented by one of the first group including a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group. The hydrocarbon of the alkyl group, the cycloalkyl group, the alkoxy group, the aryl group, the aryloxy group, the aralkyl group, the aralkoxy group, the alkenyl group, the alkenoxy group, the alkoxycarbonyl group, the acyloxy group or the acyl group of the first group may be saturated aliphatic hydrocarbon, unsaturated aliphatic hydrocarbon, alicylic hydrocarbon, aromatic hydrocarbon or the combination of the same. Further, a part or the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the second group including a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group or the like. Furthermore a hydrogen of the hydrocarbon of the alkyl group, the cycloalkyl group, the alkoxy group, the aralkoxy group, the alkenyl group, the alkenoxy group, the alkoxycarbonyl group, the acyloxy group or the acyl group of the first group may be substituted by one of the third group including a halogen atom, a silicon atom, a phosphorous atom, an alkyl group, a sulfonyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group or the like. R31 and R32, R33 and R34, R37 and R38, R39 and R310, R310 and R311, and R311 and R312 may respectively join together to form a ring. Z- represents a counter ion.

Examples of the cyan cationic dyes prior to the substitution with the organic anion include C.I. Basic blue 3, 6, 10, 12, 49, 75, 87, 95, 96, 101, 104, 107, 108, 114, 122, 124, 141, 151, 155, C.I. 51015, and the dye disclosed in Japan issued patents SHO 45-2588, SHO 47-13638, British Patent BP 13565/90, BP 18623/90, U.S. Pat. No. 2,741,605, French Patent FP 211035, German Patents GP 62367, GP 68557, GP 68558, GP 69820 and GP 71250 which is incorporated by reference.

In addition to any of these hydrophobic cationic dyes, the present invention also provides a thermal transfer ink ribbon which comprises a support and an ink layer formed thereon, characterized in that the ink layer comprises any of these hydrophobic cationic dyes.

The organic anions used in the present invention are those which can render the hydrophilic cationic dyes hydrophobic by substituting the counter ion of the cationic dye therewith. Such organic anions are those ions anionic surface active agents indicated below. It will be noted here that these organic anions may be available as salts of alkali metals prior to the substitution with the counter ion of the hydrophilic cationic dyes.

(1) Carboxylic acid anions (1a) Soaps (RCOO—)

(1b) N-Acylamino acids (RCON—COO—)

(1c) Alkyl ether carboxylic acids (RO($C_2H_4O$)$_n$COO—)

(2) Sulfonic acid anions (2a) Alkylsulfonates (RSO$_3$—)

(2b) Alkylbenzenesulfonates (formula (4))

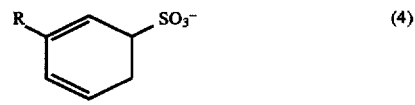

(2c) Alkylnaphthalenesulfonates (formula (5))

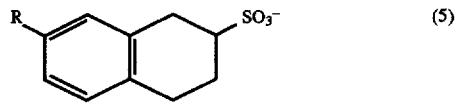

(2d) Sulfosuccinates (formula (6))

(2e) a-Olefinsulfonates (2f) N-acylsulfonates (—CON—SO$_3$—)

(3) Sulfuric ester anions (3a) Sulfated oil (3b) Alkylsulfates (ROSO$_3$—)

(3c) Alkyl ether sulfates (RO($C_2H_4O$)$_n$SO$_3$—)

(3d) Alkyl aryl ether sulfates (formula (7))

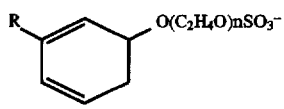 (7)

(3e) Alkylamidosulfates (RCONH—OSO$_3$—)
(4) Phosphoric ester anions
(4a) Alkylphosphates (formulas (8), (9))

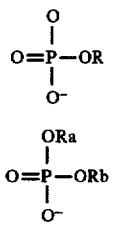

(4b). Alkyl ether phosphates (formulas (10), (11))

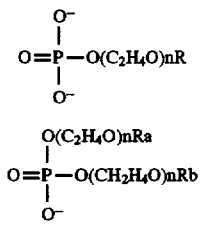

(4c) Alkyl aryl ether phosphates
(In the above organic anions, it is preferred that R, Ra and Rb, respectively, represent a linear or branched alkyl or alkenyl group having 5–20 carbon atoms from the viewpoint of the ease in availability and costs.)

Of these organic anions, it is preferable to use sulfosuccinate anions of (2d) such as diethylhexylsulfosuccinate anion, alkylbenzenesulfonate anions of (2b) such as dodecybenzenesulfonate anion, alkylsulfate anions of 3d) such as lauryl sulfate anion, and soap anions of (1a).

The hydrophobic cationic dyes of the invention can be obtained by dropping an aqueous solution of salts containing the above indicated organic anions in an aqueous solution of a hydrophilic cationic dye under agitation, extracting the resulting mixture with an organic solvent such as toluene, and removing the solvent from the organic phase to obtain a hydrophobic dye as a residue insoluble or sparingly soluble in water.

As a matter of course, the hydrophobic cationic dyes of the invention are hydrophobic in nature, so that they can be uniformly, stably, mixed with hydrophobic resins which would not be otherwise used along with known hydrophilic resins which would not be otherwise used along with known hydrophilic cationic dyes. For instance, the hydrophobic cationic dyes of the invention can be uniformly, stably mixed with hydrophobic polymer binders for use in the ink layer of a thermal transfer ink ribbon and are thus suitable for use as the dye of thermal transfer ink ribbons.

Accordingly, a thermal transfer ink ribbon composed of a support and an ink layer formed thereon wherein the ink layer contains the hydrophobic cationic dye of the invention is within the scope of the invention.

The ink layer of the thermal transfer ink ribbon of the invention may be constituted of the hydrophobic cationic dye of the invention alone. If necessary, other ingredients such as hydrophobic polymer binders, melting point adjusting agents, plasticizers, solvents, binders, and pigments and dyes other than the hydrophobic cationic dyes of the invention can be used.

The support of the thermal transfer ink ribbon of the invention may be, for example, polyethylene terephthalate films, nylon films, triacetyl cellulose films, moistureproof cellophane sheets, capacitor paper, thin paper, cloth the like.

The thermal transfer ink ribbon of the invention may be fabricated by a usual manner. For instance, an ink composition comprising the hydrophobic cationic dye of the invention is applied onto a support by use of a wire bar coater to obtain a ribbon.

In order to form color images on a transfer material by the use of the thermal transfer ink ribbon of the invention, the ink layer of the ink ribbon and the dye-receiving layer of the transfer material are placed in face-to-face relation, under which an image-forming portion is heated from the support side of the ink ribbon by means of a thermal head of a laser beam of a printer, thereby causing the dye ingredient in the ink layer to be transferred on the image-receiving layer by sublimation or thermal diffusion.

The hydrophobic cationic dyes of the invention are rendered hydrophobic by substitution of the counter ion of the hydrophilic cationic dye with an organic anion, making it possible to enhance miscibility with non-aqueous solvents and hydrophobic polymers. Thus, the dyes of the invention are usable as a dye for the thermal transfer ink ribbon.

The invention is more particularly described by way of examples.

EXAMPLE 1

Preparation of a Diethylhexylsulfosuccinate of C.I. Basic Yellow 28

1 g of C.I. Basic Yellow 28 (commercial name: Kayacryl Golden Yellow GL available from Nippon Kayaku K.K.) which is a diazacarbocyanine cationic dye for dyeing acrylic fibers from which additives such as sodium sulfate were removed by a Soxhlet apparatus using ethanol was dissolved in 100 ml of water. While agitating the dye solution, 50 g of a 2 wt % sodium diethylhexylsulfosuccinate anion).

The resultant solution was evaporated to dryness under reduced pressure. Toluene was added to the resultant residue for extraction of the dye. The toluene solution of the dye was filtered to remove an unreacted matter and side products (inorganic salts). The filtrate was concentrated to dryness under reduced pressure. As a result, about 1.6 g of the captioned hydrophobic cationic dye with a dark orange in the form of a tar was obtained.

The hydrophobic cationic dye was placed in a water-toluene phase and shaken, whereupon it was found most of the dye remained in the toluene phase. On the other hand, the dye which had not been subjected to the substitution treatment with the organic anion was kept in the aqueous phase when treated in a similar manner as set out above. This reveals that the substitution treatment contributes to drastic improvement of miscibility with organic solvents.

Fabrication of thermal transfer ink ribbon

Using the thus obtained hydrophobic cationic dye, a thermal transfer ink ribbon 10 shown in FIG. 1 was fabricated in the following manner.

A 6 μm thick polyethylene terephthalate (PET) film which had a heat-resistant, lubricating layer 1 on the one side thereof was provided as a support 2. The support 2 was applied with 25 g/m$^2$ of a thermal transfer ink composition with the following formulation on a side opposite to the side of the heat-resistant lubricating layer 1 of the support 1 and dried. By this, there was obtained a thermal transfer ink ribbon 10, as shown in FIG. 1, which had the PET film support 2 and the ink layer 3 with a thickness of about 1 μm.

Thermal transfer ink composition

| | |
|---|---|
| Hydrophopic cationic dye of the invention | |
| | 1 part by weight |
| Polyvinylbutyral | |
| | 1 part by weight |
| (6000-CS, made by Denki Chem. Ind. Co., Ltd.) | |
| Toluene | |
| | 12 parts by weight |
| Methyl ethyl ketone | |
| | 12 parts by weight |

The thermal transfer ink ribbon obtained above was set in a ribbon cassette (not shown). A color video printer (commercial name: CVP-G500, made by Sony Co., Ltd.) was used for single color printing on a printing sheet whose image-receiving layer was made of a vinyl chloride-vinyl acetate copolymer resin (commercial name: UPC-3010, made by Sony Co., Ltd.), a printing sheet whose dye-receiving layer was made of a polyester resin (commercial name: VPM-30ST, made by Sony Co., Ltd.), and a printing sheet whose dye-receiving layer was made of a cellulose ester resin (commercial name: VPM-30STA, made by Sony Co., Ltd.) As a result, there was obtained an image with a good yellow color and good gradation properties.

FIG. 2 shows a so-called dynamic sensitivity (color-development) characteristic of the ink ribbon. The abscissa axis indicates a gradation (step) which shows an energy added for image priming in a stepwise manner. As shown in the figure, the ink ribbon fabricated in this example ensures gradation printing by the thermal transfer with respect to all the printing sheets.

EXAMPLE 2

Preparation of Dodecylbenzenesulfonate of C.I. Basic Yellow 28

In the same manner as in Example 1, 1 g of C.I. Basic Yellow 28 and 1 g of sodium dodecylbenzenesulfonate were reacted to obtain about 1.8 g of crystals of the captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

In the same manner as in Example 1, the resultant hydrophobic cationic dye was used to make a thermal transfer ink ribbon, followed by a similar printing test. As a result, there was obtained an image which assumed a good yellow color and good gradation properties. FIG. 3 shows a so-called dynamic sensitivity (color-development) characteristic of the ink ribbon. As shown in the figure, the ink ribbon obtained in this example ensures gradation printing by the thermal transfer on the printing sheets.

EXAMPLE 3

Preparation of Laurylsulfate of C.I. Basic Yellow 28

In the same manner as in Example 1, 1 g of C.I. Basic Yellow 28 and 1 g of sodium laurylsulfate were reacted to obtain about 1.5 g of crystals of the captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organicolvent.

Figure 4:
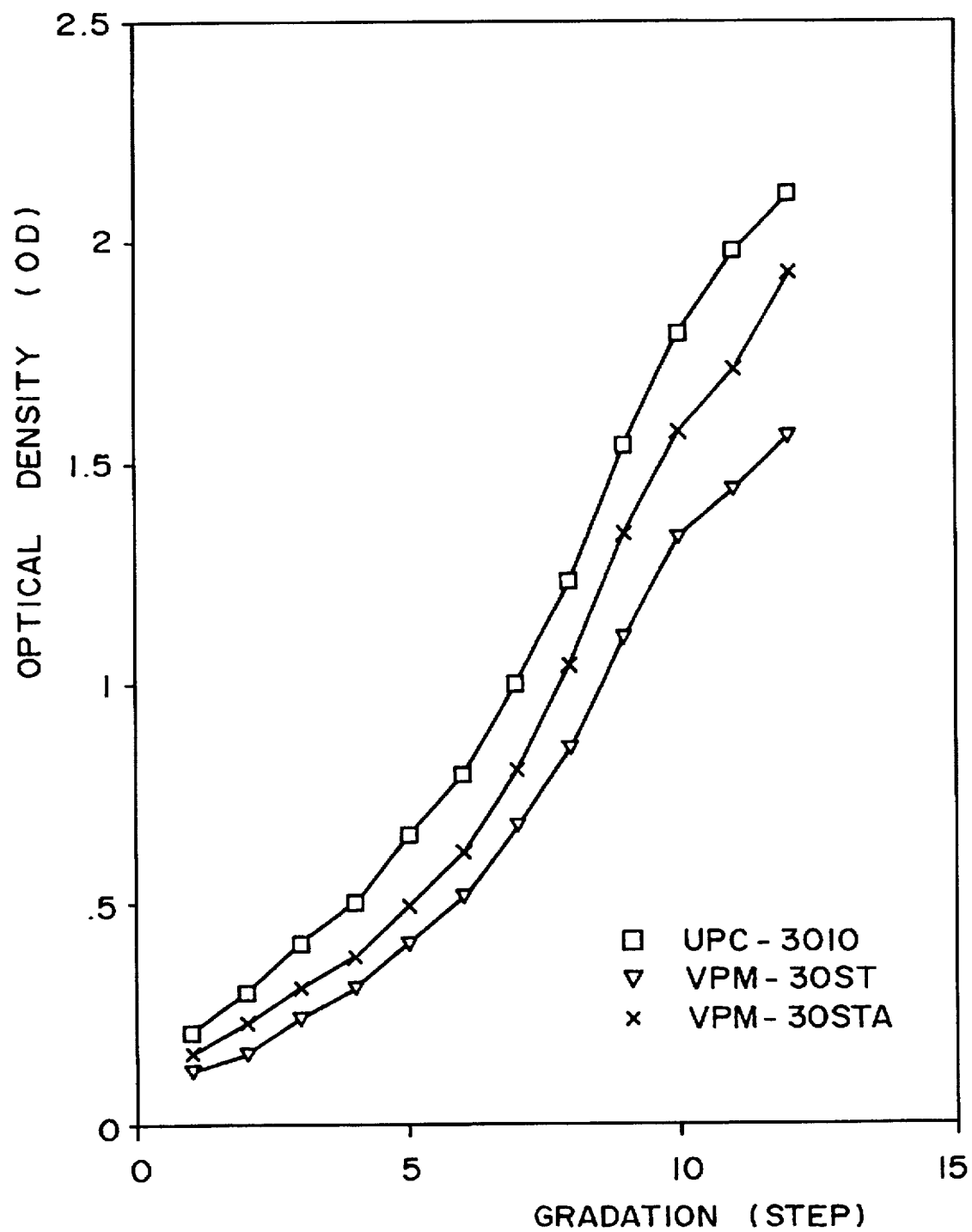
FIG. 4 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good yellow color and good gradation properties. FIG. 4 shows a so-called dynamic sensitivity (color-development) characteristic of the ink ribbon. As shown in the figure, the ink ribbon obtained in this example ensures gradation printing by the thermal transfer on the printing sheets.

EXAMPLE 4

Preparation of Laurylsulfate of C.I. Basic Yellow 51

In the same manner as in Example 1, 1 g of C.I. Basic Yellow 51 (commercial name: Diacryl Yellow 3G-N, made by Mitsubishi Chem. Hoechest Co., Ltd.) and 1 g of sodium dodecylbenzenesulfonate were reacted to obtain about 1.5 g of crystals of the captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

Figure 5:
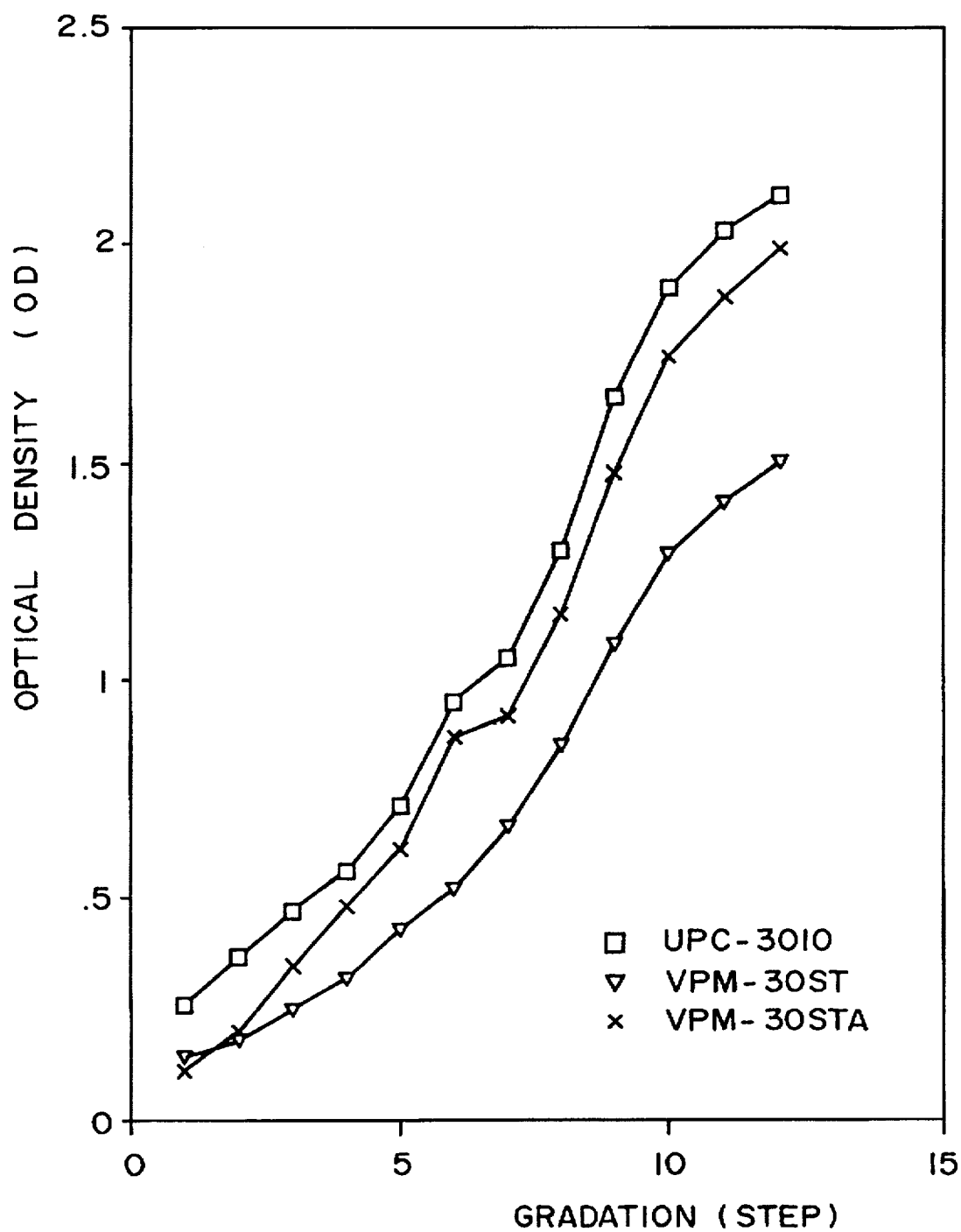
FIG. 5 is a dynamic sensitivity characteristic graph of still another ink ribbon of the invention.

In the same manner as in Example 1, the resultant hydrophobic cationic dye was used to make a thermal transfer ink ribbon, following by a similar printing test. As a result, there was obtained an image which assumed a good lemon yellow color and good gradation properties. FIG. 5 shows a so-called dynamic sensitivity (color-development) characteristic of the ink ribbon. As shown in the figure, the ink ribbon obtained in this example ensures gradation printing by the thermal transfer on the printing sheets.

EXAMPLE 5

Preparation of Laurylsulfate of C.I. Basic Yellow 21

In the same manner as in Example 1, 1 g of C.I. Basic Yellow 21 (commercial name: Aizen Cathilon Yellow 7GLH, made by Hodogaya Chem. Inc. Co., Ltd.) and 1 g of sodium dodecylbenzenesulfonate were reacted to obtain about 1.6 g of crystals of the captioned hydrophobic cationic dye. The hydrophobic cationic dye was placed in water-toluene phase and shaken, whereupon the dye mostly remained in the toluene phase. This reveals that the substitution with the organic anion contributes to drastically improved miscibility with the organic solvent.

Figure 6:
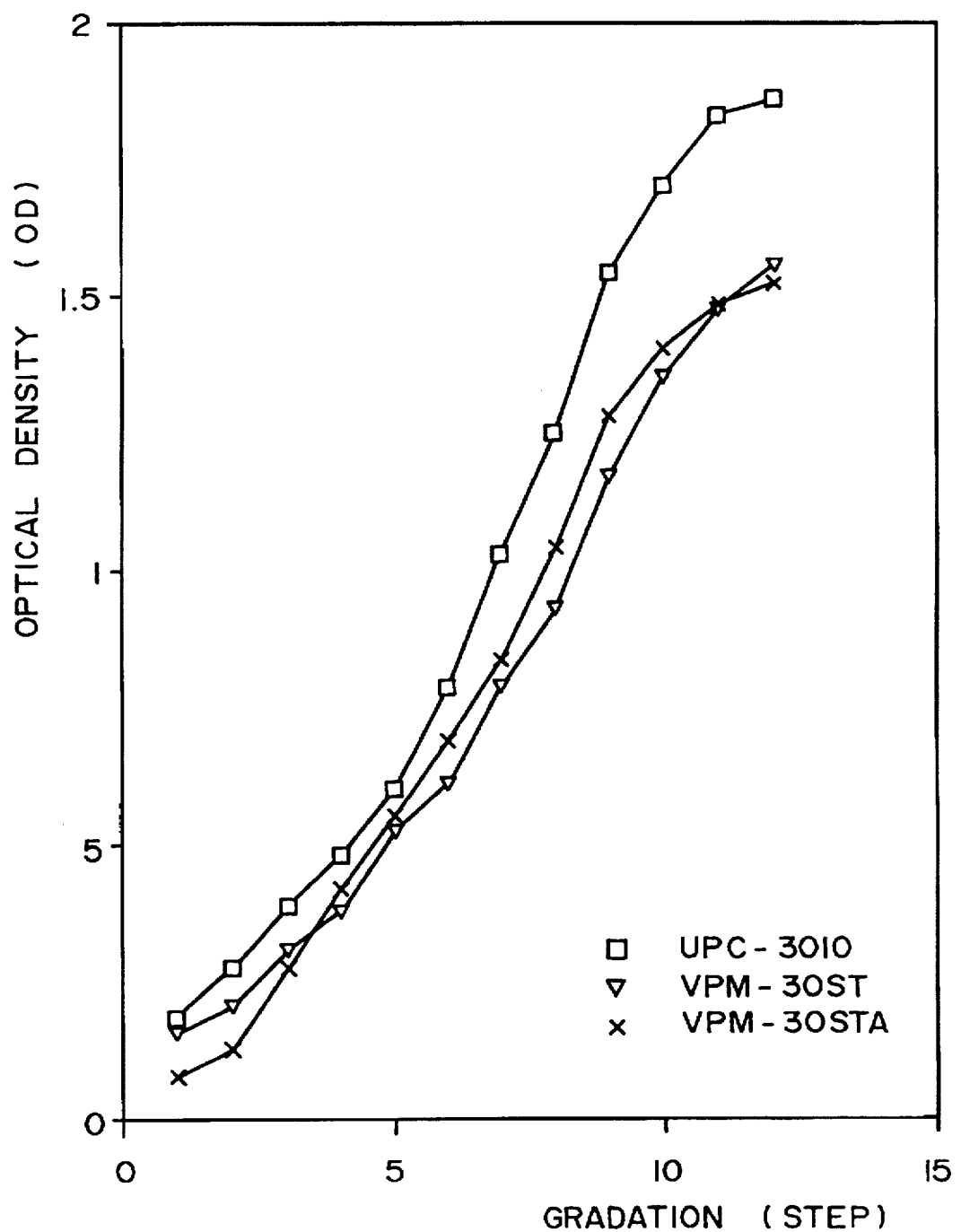
FIG. 6 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good lemon yellow color and good gradation properties. FIG. 6 shows a so-called dynamic sensitivity (color-development) characteristic of the ink ribbon. As shown in the figure, the ink ribbon obtained in this example ensures gradation printing by the thermal transfer on the printing sheets.

EXAMPLE 6

Preparation of Diethylhexylsulfosuccinate of C.I. Basic Yellow 36

In the same manner as in Example 1, 1 g of C.I. Basic Yellow 36 (commercial name: Aizen Cathilon Yellow K-3RLH, made by Hodogaya Chem. Inc. Co., Ltd.) and 1 g of sodium diethylhexylsuccinate were reacted to obtain about 1.8 g of a tar-like captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

Figure 7:
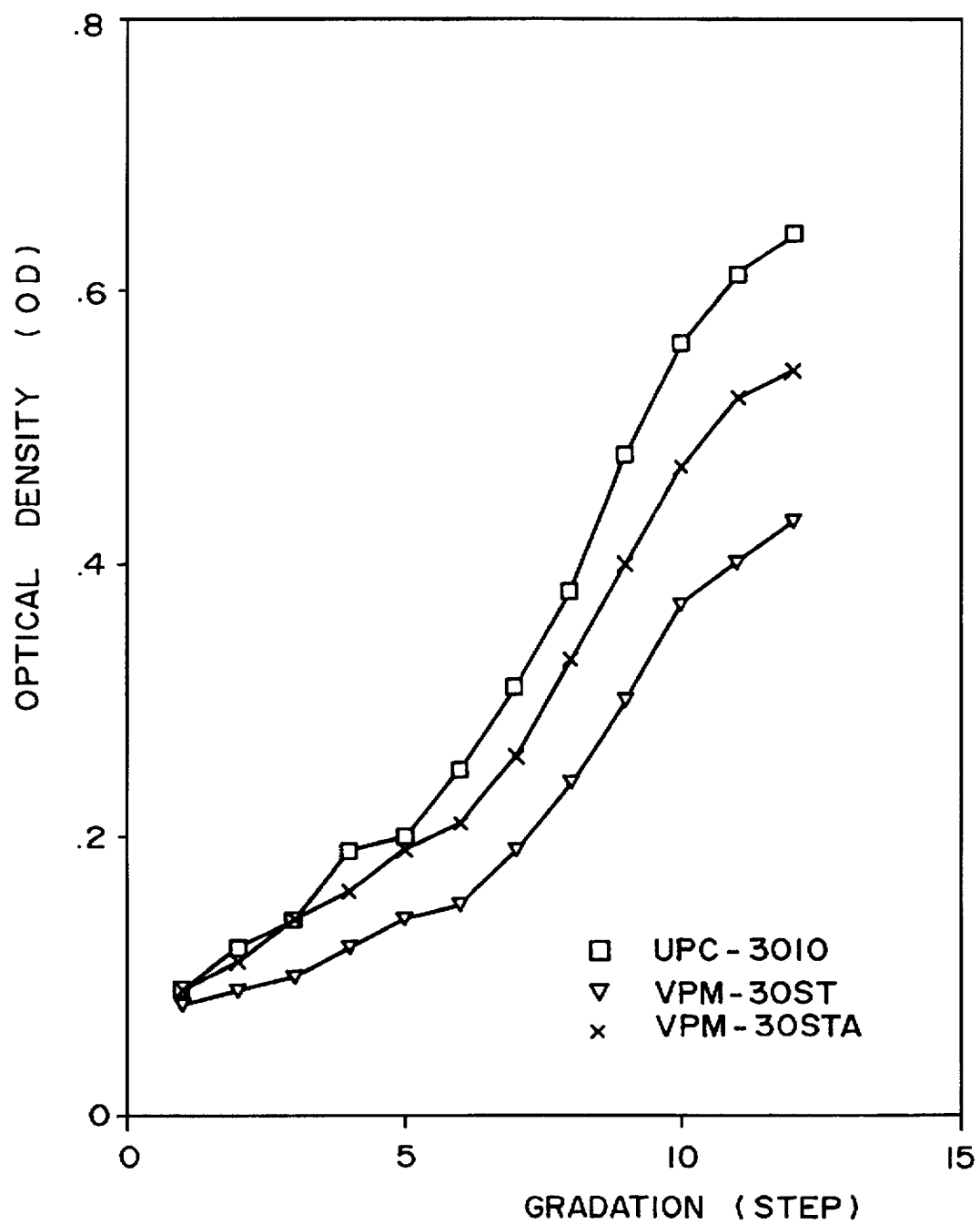
FIG. 7 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good yellow color and good gradation properties. FIG. 7 shows a so-called dynamic sensitivity (color-development) characteristic of the ink ribbon. As shown in the figure, the ink ribbon obtained in this example ensures gradation printing by the thermal transfer on the printing sheets.

EXAMPLE 7

Preparation of Laurylsulfate of C.I. Basic Yellow 67

In the same manner as in Example 1, 1 g of C.I. Basic Yellow 67 (Commercial name: Kayacryl Yellow 3RL, made by Nippon Kayaku K.K.) and 1 g of sodium laurylsulfate were reacted to obtain about 1.8 g of a tar-like captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

Figure 8:
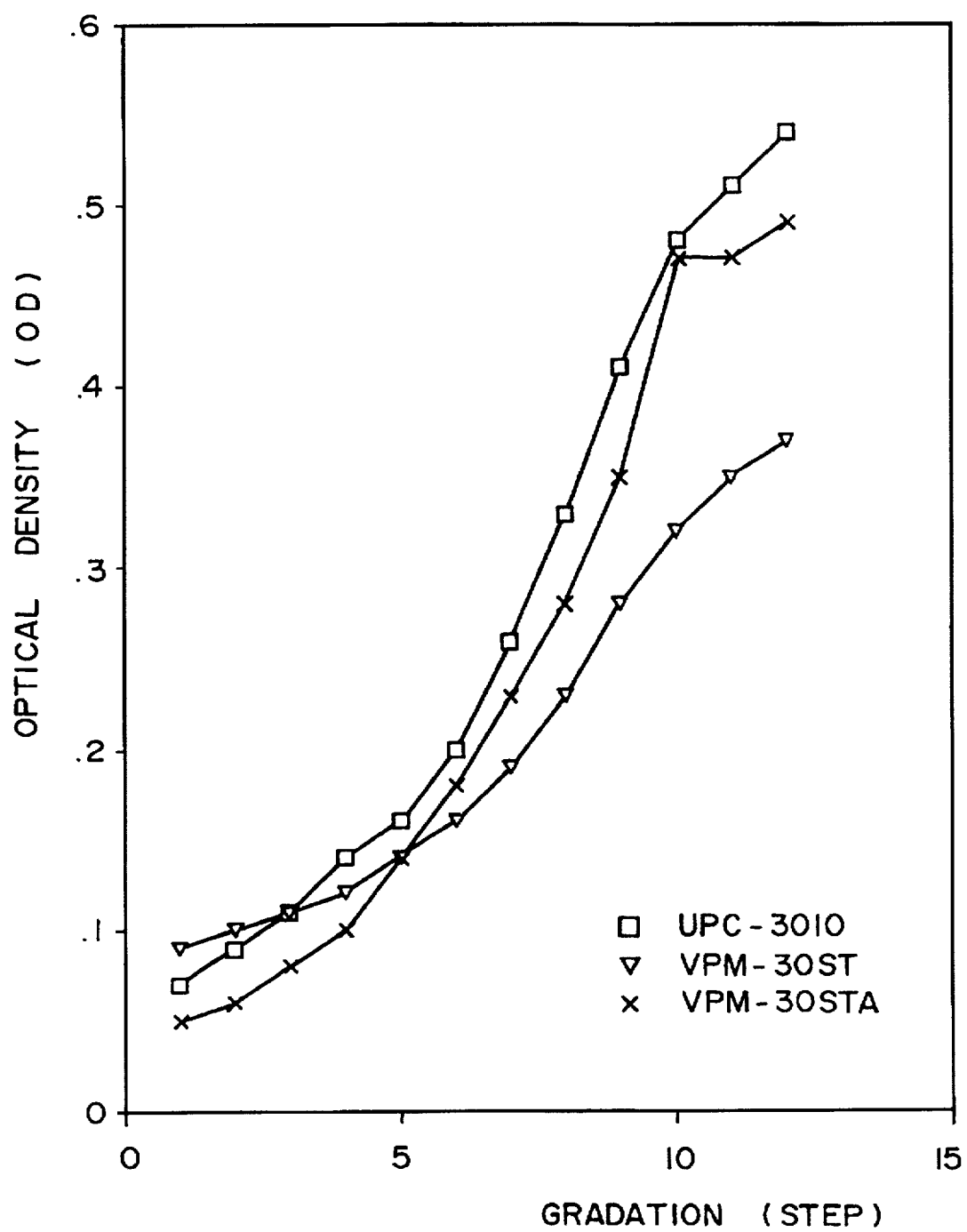
FIG. 8 is a dynamic sensitivity characteristic graph of yet another ink ribbon of the invention.

In the same manner as in Example 1, the resultant hydrophobic cationic dye was used to make a thermal transfer ink ribbon, followed by a similar printing test. As a result, there was obtained an image which assumed a good yellow color and good gradation properties. FIG. 8 shows a so-called dynamic sensitivity (color-development) characteristic of the ink ribbon. As shown in the figure, the ink ribbon obtained in this example ensures gradation printing by the thermal transfer on the printing sheets.

EXAMPLE 8

Preparation of Laurylsulfate of C.I. Basic Yellow 73

In the same manner as in Example 1, 1 g of C.I. Basic Yellow 73 (commercial name: Aizen Cathilon Yellow CD-RLH, made by Hodogaya Chem. Ind. Co., Ltd.) and 1 g of sodium laurylsulfate were reacted to obtain about 1.8 g of a tar-like captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

Figure 9:
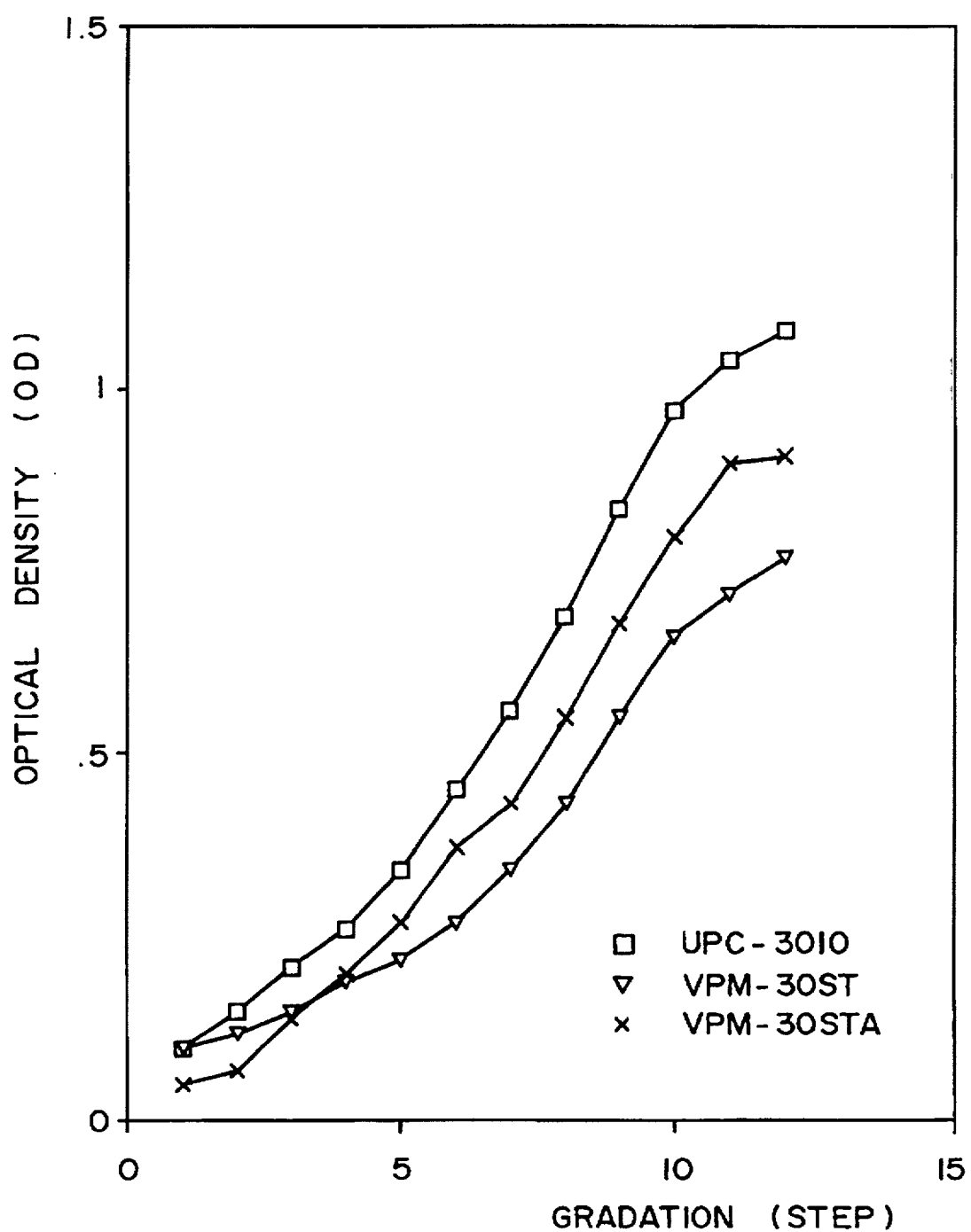
FIG. 9 is a dynamic sensitivity characteristic graph of another ink ribbon of the invention.
Figure 10:
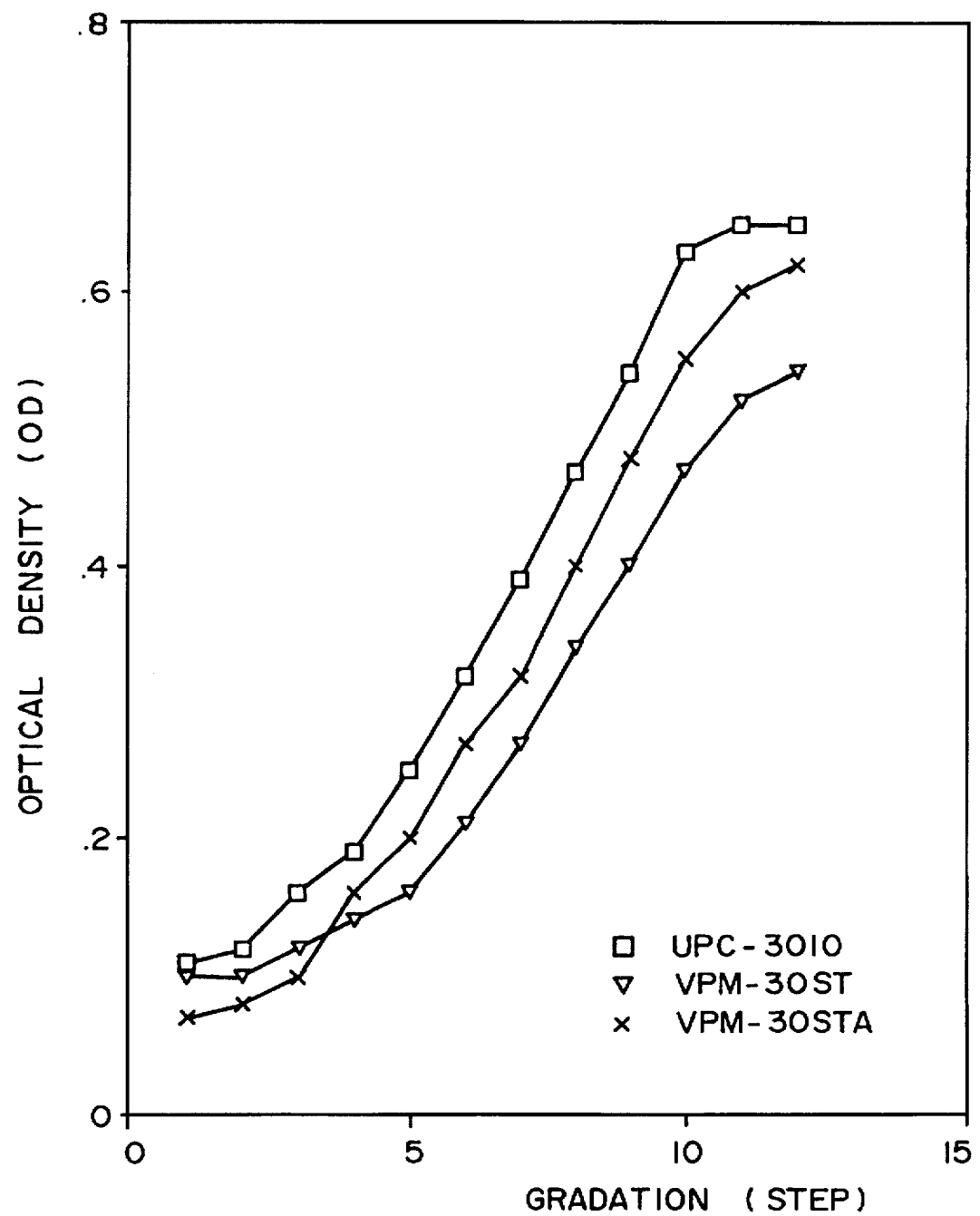
FIG. 10 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good yellow color and good gradation properties. FIG. 9 shows a so-called dynamic sensitivity (color-development) characteristic of the ink ribbon. As shown in the figure, the ink ribbon obtained in this example ensures gradation printing by the thermal transfer on the printing sheets.

EXAMPLE 9

Preparation of Dodecylbenzenesulfonate od C.I. Basic Yellow 14

In the same manner as in Example 1, 1 g of C.I. Basic Red 14 (commercial name: Aizen Cathilon Red 4GH, made by Hodogaya Chem. Ind., Col, Ltd.) and 1 g of sodium dodecylbenzenesulfonate were reacted to obtain about 1.6 g of a dark reddish purple tar-like captioned hydrophobic cationic dye. The hydrophobic cationic dye was placed in a water-toluene phase and shaken, whereupon the dye mostly remained in the toluene phase. This reveals that the substitution with the organic anion contributes to drastically improved miscibility with the organic solvent.

In the same manner as in Example 1, the resultant hydrophobic cationic dye was used to make a thermal transfer ink ribbon, following by a similar printing test. As a result, there was obtained an image which assumed a good yellow color and good gradation properties. FIG. 9 shows a so-called dynamic sensitivity (color-development) characteristic of the ink ribbon. As shown in the figure, the ink ribbon obtained in this example ensures gradation printing by the thermal transfer on the printing sheets.

EXAMPLE 10

Preparation of Dietylhexylsulfosuccinate of C.I. Basic Red 13

In the same manner as in Example 1, 1 g of C.I. Basic Red 13 (commercial name: Aizen Cathilon Pink FGH, made by Hodogaya Chem. Ind., Col, Ltd.) and 1 g of sodium diethylhexylsuccinate were reacted to obtain about 1.8 g of a tar-like captioned hydrophobic cationic dye. The hydrophobic cationic dye was placed in a water-toluene phase and shaked, whereupon the due mostly remained in the toluene phase. This reveals that the substitution with the organic anion contributes to drastically improved miscibility with the organic solvent.

Figure 11:
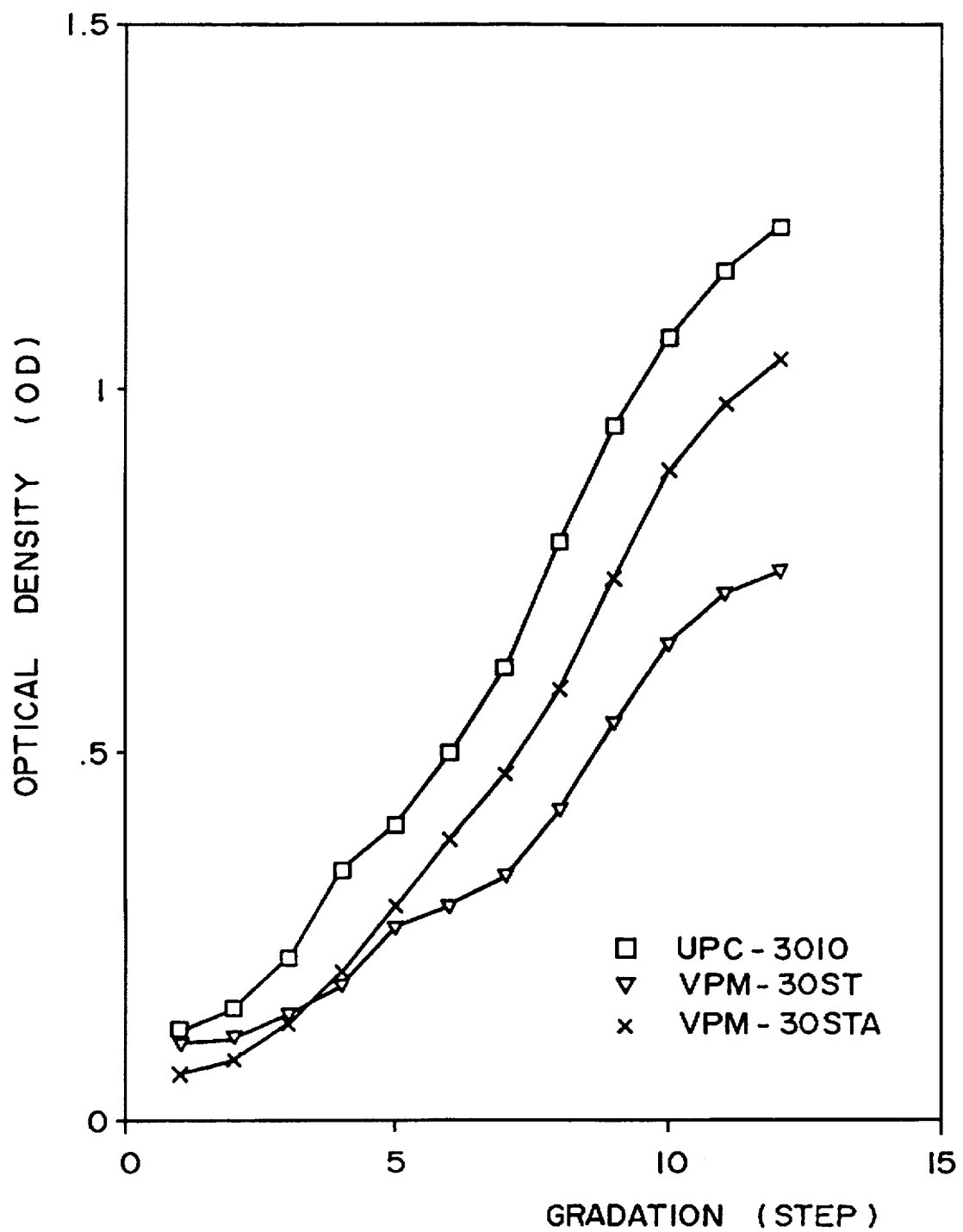
FIG. 11 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good magenta color and good gradation properties. FIG. 11 shows a so-called dynamic sensitivity (color-development) characteristic of the ink ribbon. As shown in the figure, the ink ribbon obtained in this example ensures gradation printing by the thermal transfer on the printing sheet.

EXAMPLE 11

Preparation of Dodecylbenzenesulfonate of C.I. Basic Violet 7

In the same manner as in Example 1, 1 g of C.I. Basic Violet 7 (commercial name: Aizen Cathilon Red 6GH, made by Hodogaya Chem. Ind. Co., Ltd.) and 1 g. of sodium dodecylbenzenesulfonate were reacted to obtain about 1.8 g of the captioned hydrophobic cationic dye. The hydrophobic cationic dye was placed in a water-toluene phase and shaken, whereupon the dye mostly remained in the toluene phase. This reveals that the substitution of the counter ion with the organic anion contributes to drastically improved miscibility with the organic solvent.

Figure 12:
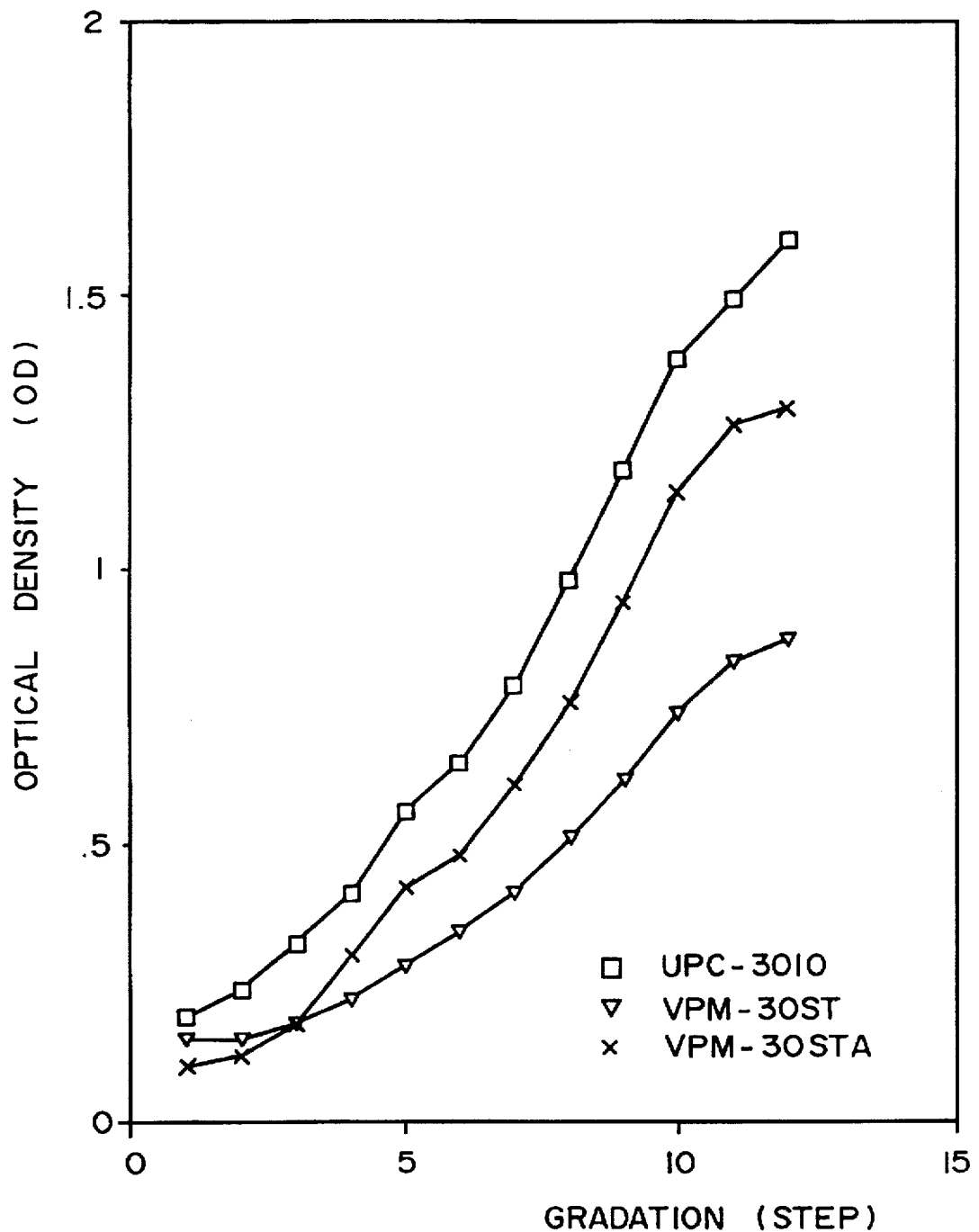
FIG. 12 is a dynamic sensitivity characteristic graph of another ink ribbon of the invention.

In the same manner as in Example 1, the resultant hydrophobic cationic dye was used to make a thermal transfer ink ribbon, followed by a similar printing test. As a result, there was obtained an image which assumed a good magenta color and good gradation properties. FIG. 12 shows a so-called dynamic sensitivity (color-development) characteristic of the ink ribbon. As shown in the figure, the ink ribbon obtained in this example ensures gradation printing by the thermal transfer on the printing sheets.

EXAMPLE 12

Preparation of Dietylhexylsulfosuccinate of C.I. Basic blue 75

In the same manner as in Example 1, 1 g of C.I. Basic Blue 75 (commercial name:Kayacryl Light Blue 4GSL, made by Nippon Kayaku K.K.) and 1 g of sodium diethylhexylsuccinate were reacted to obtain about 1.6 of a dark bluish green tar-like captioned hydrophobic cationic dye. The hydrophobic cationic dye was placed in a water-toluene phase and shaken, whereupon the dye mostly remained in the toluene phase. This reveals that the substitution with the organic anion contributes to drastically improving miscibility with the organic solvent.

Figure 13:
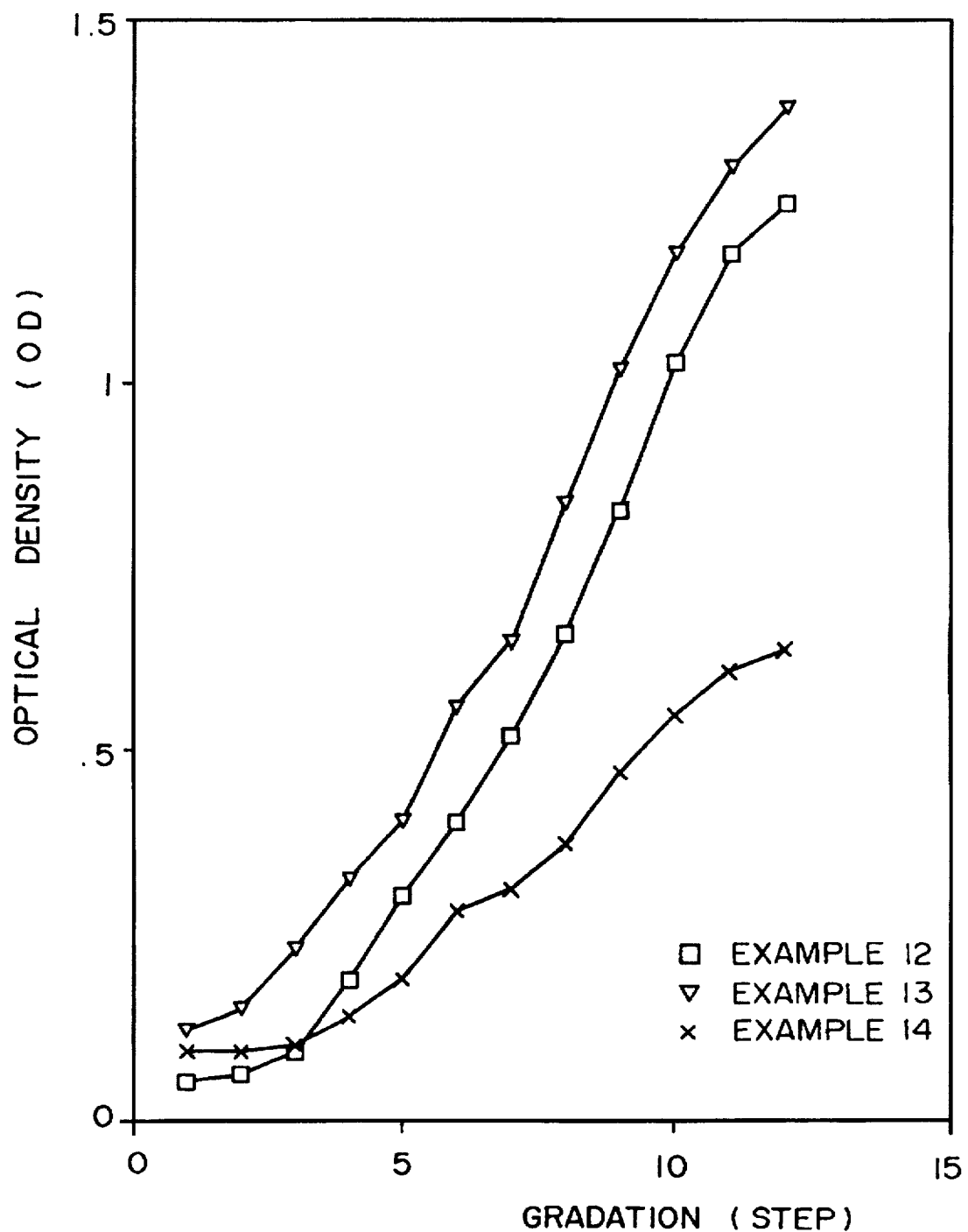
FIG. 13 is a dynamic sensitivity characteristic graph of another ink ribbon of the invention.

In the same manner as in Example 1, the resultant hydrophobic cationic dye was used to make a thermal transfer ink ribbon, followed by a similar printing test using a printing sheet (VMP-30STA) of Sony Co., Ltd. As a result, there was obtained an image which assumed a good cyan color and good gradation properties. FIG. 13 shows a so-called dynamic sensitivity (color-development) characteristic of the ink ribbon. As shown in the figure, the ink ribbon obtained in this example ensures gradation printing by the thermal transfer on the printing sheets.

EXAMPLE 13

Preparation of Dodecylbenzenesulfonate of C.I. Basic Blue 3

In the same manner as in Example 1, 1 g of C.I. Basic Violet 7 (commercial name: Aizen Cathilon Pure Blue 5GH, made by Hodogaya Chem. Ind. Co., Ltd.) and 1 g of sodium dodecylbenzenesulfonate were reacted to obtain about ⅛ g of crystals of the captioned hydrophobic cationic dye. The hydrophobic cationic dye was placed in a water-toluene phase and shaken, whereupon the dye mostly remained in the toluene phase. This reveals that the substitution of the counter ion with the organic anion contributes to drastically improved miscibility with the organic solvent.

In the same manner as in Example 13, the resultant hydrophobic cationic dye was used to make a thermal transfer ink ribbon, followed by a similar printing test. As a result, there was obtained an image which assumed a good cyan color and good gradation properties. FIG. 13 shows a so-called dynamic sensitivity (color-development characteristic of the ink ribbon. As shown in the figure, the ink ribbon obtained in this example ensures gradation printing by the thermal transfer on the printing sheets.

EXAMPLE 14

Preparation of Laurylsulfate of C.I. Basic Blue 3

In the same manner as in Example 1, 1 g of C.I. Basic Violet 7 (commercial name: Aizen Cathilon Pure Blue 5GH, made by Hodogaya Chem. Ind. Co., Ltd.) and 1 g of sodium laurylsulfate were reacted to obtain about 1.8 g of crystals of the captioned hydrophobic cationic dye. The hydrophobic cationic dye was placed in a water-toluene phase and shaken, whereupon the dye mostly remained in the toluene phase. This reveals that the substitution of the counter ion contributes to drastically improved miscibility with the organic solvent.

In the same manner as in Example 12, the resultant hydrophobic cationic dye was used to make a thermal transfer ink ribbon, followed by a similar printing test using a printing sheet (UPC-3010) of Sony Co., Ltd. As a result, there was obtained an image which assumed a good cyan color and good gradation properties. FIG. 13 shows a so-called cynamic sensitivity (color-development) characteristic of the ink ribbon. As shown in the figure, the ink ribbon obtained in this example ensures gradation print the thermal transfer on the printing sheets.

Since the cationic dyes of the invention are hydrophobic in nature, they can be mixed with hydrophobic polymers satisfactorily and uniformly with good storage stability. Accordingly, when the hydrophobic cationic dyes of the invention and hydrophobic polymers are used to form an ink layer of a thermal transfer ink ribbon, the sensitivity at the time of the transfer and the color and light fastness of the resultant images can be improved.

What is claimed is:

1. A thermal transfer ink ribbon comprising a support and an ink layer formed on said support, wherein said ink layer comprises a hydrophobic cationic dye which is obtained by substituting, with an ion of an anionic surface active agent a counter ion of a diazacarbocyanine cationic dye of the formula (1),

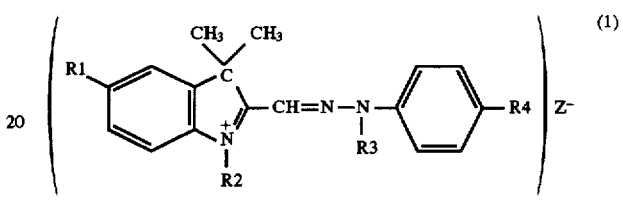

wherein R1, R2, R3 and R4 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of a second group comprising of a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of the third group comprising of a halogen atom, a silicon atom, aphosphorous atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group, Z- represents a counter ion.

2. A thermal transfer ink ribbon comprising a support and an ink layer formed thereon, wherein said ink layer comprises a hydrophobic cationic dye which is obtained by substituting a counter ion of a cationic dye of C.I. Basic Yellow 21, 36, 67 or 73 with an ion of an anionic surface active agent.

3. A thermal transfer ink ribbon comprising a support and an ink layer formed on said support, wherein said ink layer comprises a hydrophobic cationic dye obtained by substituting, with an ion of an anionic surface active agent, a counter ion of a hemicyanine cationic dye of the formula (2),

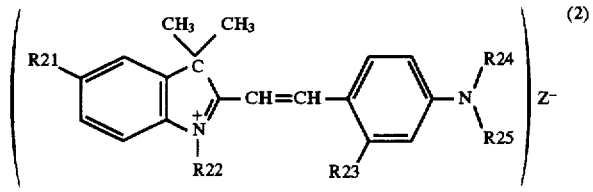

wherein R21, R22, R23, R24 and R25 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of a second group comprising a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of the third group comprising a halogen atom, a silicon atom, a phosphorus atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group, R24 and R25 may join together to form a ting, Z- represents a counter ion.

4. A thermal transfer ink ribbon comprising a support and an ink layer formed on said support, wherein said ink layer comprises a hydrophobic cationic dye which is obtained by substituting, with an ion of an anionic surface active agent, a counter ion of an oxazine cationic dye of the formula (3a) or (3b),

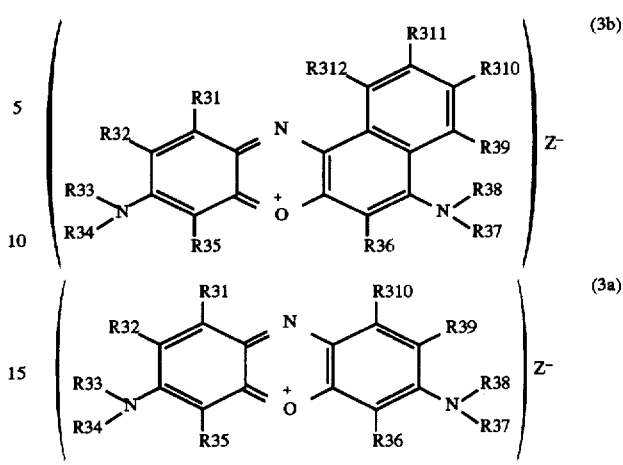

wherein R31, R32, R33, R34, R35, R36, R37, R38, R39, R310, R311 and R312 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of a second group comprising a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of the third group comprising a halogen atom, a silicon atom, a phosphorous atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an amide group, imino group, cyano group, ketone group or an acyl group, R31 and R32, R33 and R34, R37 and R38, R39 and R310, R310 and R311, and R311 and R312 may respectively join together to form a ring, Z- represents a counter ion.

5. A thermal transfer ink ribbon comprising:
a support having an ink layer disposed thereon, said ink layer comprising a hydrophobic cationic dye including a cationic dye portion and a hydrophobic anionic surface active agent portion, said cationic dye portion being selected from the group consisting of a diazacarbocyanine dye cation, a hemicyanine dye cation and an oxazine dye cation having the formula 3a or 3b, as follows:

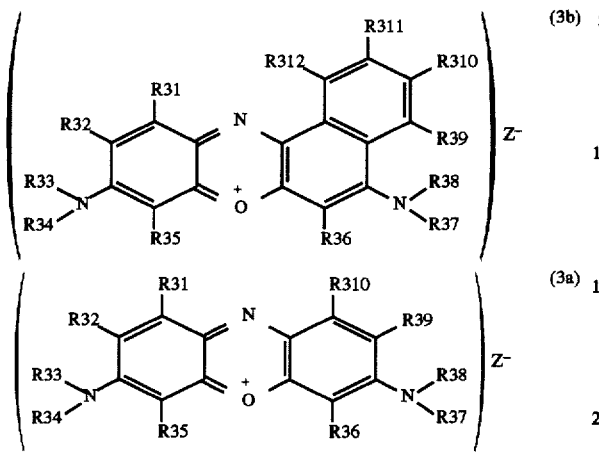

wherein R31, R32, R33, R34, R35, R36, R37, R38, R39, R310, R311 and R312 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group or said first group may be substituted by one of a second group comprising a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of the third group comprising said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said second group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said third group, R31 and R32, R33 and R34, R37 and R38, R39 and R310, R310 and R311, and R311 and R312 may respectively join together to form a ring, Z- represents a counter ion.

6. A thermal transfer ink ribbon comprising:
a support having an ink layer thereon, said ink layer comprising a hydrophobic cationic dye obtained by exchanging an inorganic counter anion in a cationic dye with a hydrophobic surface active agent anion, wherein the starting cationic dye before exchange is selected from the group consisting of:

(a) a diazacarbocyanine cationic dye having the formula (1):

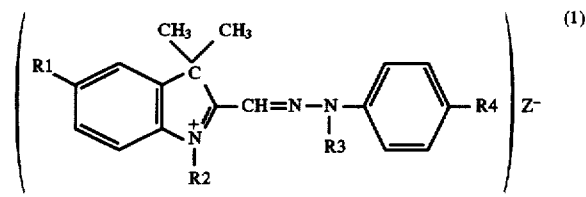

wherein
R1, R2, R3 and R4 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of a second group comprising a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of the third group comprising a halogen atom, a silicon atom, aphosphorous atom, an alkyl group, a cycloalkyl group, a hydroxyl group, a sulfate group, a sulfonyl group, an alkoxy group, an aryl group, an aralkyl group, an aryloxy group, an aralkoxy group, an alkenyl group, an alkenoxy group, an alkoxycarbonyl group, an acyloxy group, a carboxyl group, an aldehyde group, an alkoxy group, imino group, cyano group, ketone group or an acyl group, Z- represents a counter ion,
(b) C.I. Basic Yellow 21, 26, 67 or 73;
(c) a hemicyanine dye of the formula (2)

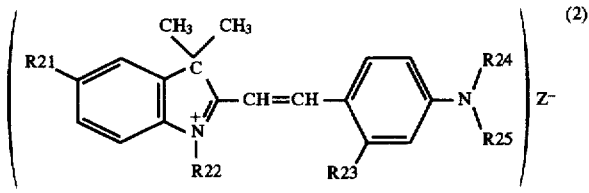

wherein R21, R22, R23, R24 and R25 are independently represented by one of said first group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said second group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said third group, R24 and R25 may join together to for a ring, Z- represents a counter ion, (d) an oxazine cationic dye of the formula 3a or 3b

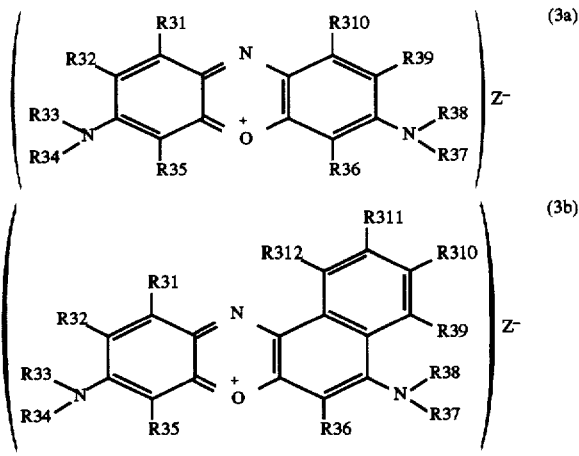

wherein R31, R32, R33, R34, R35, R36, R37, R38, R39, R310, R311 and R312 are independently represented by one of a first group comprising a hydrogen atom, a halogen atom, a cyano group, an alkyl group, a cycloalkyl group, an alkoxy group, an aryl group, an aryloxy group, an aralkyl group, an aralkoxy group, an alkenyl group, an alkenoxy group, an alkoxycarbonyl group, an acyloxy group or an acyl group, a hydrocarbon of said alkyl group, said cycloalkyl group, said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group or said first group may be substituted by one of a second group comprising a halogen atom, a silicon atom, a phosphorous atom, a hydroxyl group, a sulfate group, a sulfonyl group, an alkoxy group, an aryloxy group, an aralkoxy group, an alkenoxy group, an alkoxycarbonyl group, an acyloxy group, a carboxyl group, an aldehyde group, an amide group, imino group, cyano group, ketone group or an acyl group, a hydrogen of said hydrocarbon of said alkyl group, said cycloalkyl group, said alkoxy group, said aralkyl group, said alkenyl group, said alkenoxy group, said alkoxycarbonyl group, said acyloxy group or said acyl group of said first group may be substituted by one of the third group comprising said alkoxy group, said aryl group, said aryloxy group, said aralkyl group, said aralkoxy group, said alkenyl group, said alkenoxy group, said alkoxycarbonyl group, said acyloxy group or said acyl group of said first group may be saturated aliphatic hydrocarbon, unsaturated aliphatic hydrocarbon, alicylic hydrocarbon, aromatic hydrocarbon or a combination of said saturated aliphatic hydrocarbon, said unsaturated aliphatic hydrocarbon, said alicylic hydrocarbon or said aromatic hydrocarbon, a part of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said second group, a hydrogen of said hydrocarbon of said alkyl group, said cycloalkyl group, said alkoxy group, said aralkoxy group, said alkenyl group, said alkenoxy group, said alkoxycarbonyl group, said acyloxy group or said acyl group of said first group may be substituted by one of said third group, R31 and R32, R33 and R34, R37 and R38, R39 and R310, R310 and R311, and R311 and R312 may respectively join together to form a ring, Z- represents a counter ion.

7. A thermal transfer ink ribbon according to claim 6 wherein said organic anion is one selected from the group consisting of a carboxylic acid anion, a sulfonic acid anion, a sulfuric ester anion and phosphoric ester anion.

* * * * *